United States Patent [19]

Tonelli

[11] Patent Number: 4,939,096

[45] Date of Patent: Jul. 3, 1990

[54] METHOD AND APPARATUS FOR ASSAYING WHOLE BLOOD

[75] Inventor: Quentin J. Tonelli, Portland, Me.

[73] Assignee: Idexx, Corp., Portland, Me.

[21] Appl. No.: 905,856

[22] Filed: Sep. 10, 1986

[51] Int. Cl.⁵ ..................... C12Q 1/70; G01N 33/538
[52] U.S. Cl. ........................................ 435/5; 435/2;
435/7; 435/30; 435/34; 435/805; 436/541;
436/825; 422/61
[58] Field of Search ................... 435/7, 30, 34, 810,
435/805, 2, 5; 436/541, 825; 422/61

[56] References Cited

U.S. PATENT DOCUMENTS

| | | | |
|---|---|---|---|
| 3,552,925 | 1/1971 | Fetter | 436/63 |
| 3,763,879 | 10/1973 | Jaworek | 137/268 |
| 3,825,410 | 7/1974 | Bagshawe | 436/536 |
| 3,929,583 | 12/1975 | Sharpe | 435/292 |
| 3,963,119 | 6/1976 | Lukacs | 206/216 |
| 3,972,812 | 8/1976 | Gresl | 210/77 |
| 4,090,850 | 5/1978 | Chen | 436/530 |
| 4,111,807 | 9/1978 | Boomus | 210/152 |
| 4,301,010 | 11/1981 | Eddleman | 210/406 |
| 4,397,955 | 8/1983 | Entis | 435/292 |
| 4,406,786 | 9/1983 | Hein | 210/223 |
| 4,424,279 | 1/1984 | Bohn et al. | 436/808 |
| 4,503,143 | 3/1985 | Gerber | 435/7 |
| 4,594,327 | 6/1986 | Zuk | 436/530 |
| 4,632,901 | 12/1986 | Valkirs et al. | 435/5 |
| 4,727,019 | 2/1988 | Valkirs et al. | 435/5 |

FOREIGN PATENT DOCUMENTS

| | | | |
|---|---|---|---|
| 140337 | 5/1985 | European Pat. Off. | 435/7 |
| 0190488 | 5/1985 | European Pat. Off. | |
| 143574 | 6/1985 | European Pat. Off. | 435/7 |
| 159727 | 10/1985 | European Pat. Off. | 435/7 |
| 2344842 | 3/1977 | France | |
| 2105210 | 8/1962 | United Kingdom | 435/292 |
| 79/01120 | 12/1980 | World Int. Prop. O. | |

OTHER PUBLICATIONS

Entis et al. (1982), J. Food Protect, 45:8–11.
Entis et al. (1982), Appl. and Env. Microbiol., 43:261–68.
New Brunswick Scientific Co. Ad–"The Iso–Grid System".
Brodsky et al. (1982), J. Food Protect., 45:292–96.
Brodsky et al. (1982), J. Food Protect., 45:301–04.
Innovative Products for Separation Science Ad.
Chem. Abstracts (1985), vol. 102, p. 484, Abstract No. 22174m.
G. Arterioscler. (1983) (Suppl. 2), pp. 87–94 (AR''').
Snyder et al., "Activation of Complement by Blood Transfusion Filters", Vox Sang., 45:288–293 (1983).

Primary Examiner—Christine M. Nucker

[57] ABSTRACT

A method of assaying a sample of whole blood for one member of a specific binding pair, the method involving treating the sample with salt to alter the red blood cells in the sample to decrease their ability to pass through filter media, exposing the resulting sample to a filter which retains the red blood cells but allows the passage therethrough of filtrate of the sample containing the member of the specific binding pair, and measuring the member of the filtrate.

18 Claims, 1 Drawing Sheet

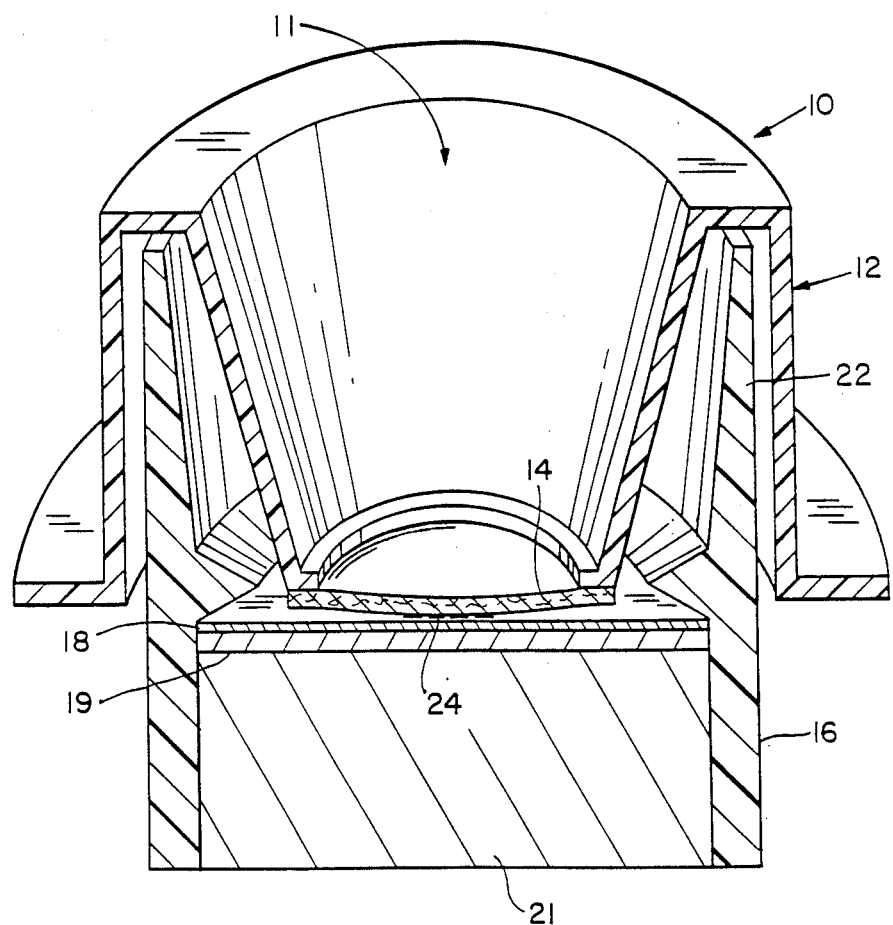

METHOD AND APPARATUS FOR ASSAYING WHOLE BLOOD

BACKGROUND OF THE INVENTION

This invention relates to the performance of immunoassays on whole blood.

Immunoassays are carried out to detect a particular antigen, hapten, or antibody in blood. Since red blood cells interfere with such assays, they are normally removed from the blood prior to performing the assay, for example, by centrifugation or filtration. The resulting plasma solution can then be used in any standard immunoassay, e.g., as described by Gerber et al. U.S. Pat. No. 4,503,143, hereby incorporated by reference, which describes a colorimetric method of detection of bindable substances such as antigens, using chromogenic agents such as tetramethyl benzidine.

SUMMARY OF THE INVENTION

In general, the invention features a method of assaying a sample of whole blood for one member of a specific binding pair, involving treating the sample with a salt to alter the red blood cells in the sample to decrease their ability to pass through filter media, exposing the resultant sample to a filter which retains the red blood cells but allows the passage therethrough of filtrate containing the member of the specific binding pair being assayed, and measuring the member of the filtrate. As used herein, the term "specific binding pair" means any pair of molecules which bind to each other but do not bind to a significant degree to other molecules; examples of such pairs are antigens and antibodies specific therefor.

It is believed that the salt causes the red blood cells in the sample to exhibit a change in physical properties, e.g., deformability, so that they are unable to pass through filter media which would have permitted their passage prior to treatment with the salt. A filter having an average pore size small enough to retain untreated red blood cells would become clogged and prevent passage of liquid as well. According to the invention, a filter can be used which has an average pore size (nominal size 0.3-0.6 microns) large enough to prevent clogging, but which still retains the treated red blood cells.

In preferred embodiments of the method, the step of treating the sample with a salt involves mixing the sample with a hypertonic solution to form a dilute solution, and following the exposing of the sample to the filter, the filtrate is deposited on a solid support on which the measuring of the member of the specific binding pair is carried out; preferably, the solid support and the filter are in contact with one another when the sample is exposed to the filter. Preferably, the hypertonic solution contains a salt of ionic strength of at least 0.5M.

The method of the invention is preferably carried out using a kit composed of a first container holding a hypertonic solution, a second container for holding the hypertonic solution and mixing it with the sample, a filter positioned with respect to the second container so as to permit the mixture of the sample and the hypertonic solution to pass from the container through the filter, such filter being capable of retaining the treated red blood cells in the sample, and means e.g., a solid support, for collecting the sample after it has passed through the filter.

The invention allows the rapid and simple assay of whole blood samples for any immunologically detectable compound, without prior removal of red blood cells.

Other features and advantages of the invention will be apparent from the following description of the preferred embodiments thereof, and from the claims.

DESCRIPTION OF THE PREFERRED EMBODIMENT

The FIGURE is a diagrammatic representation of an assay filter assembly of the invention.

STRUCTURE

Referring to the FIGURE, cylindrical membrane assembly 10 includes filter holder 12 fitted with filter 14 to form fluid chamber 11, and an assay membrane holder 16 fitted with assay membrane 18. Membrane holder 16 and filter holder 12 may be constructed of any suitable nonporous material, for example, PVC.

Filter holder 12 has an annular groove which mates with annular ridge 22 on assay membrane holder 16 so that filter 14 is positioned in intimate and homogeneous contact with assay membrane 18, which is supported by porous support disc 19, which in turn overlies absorbent bed 21. Assay membrane 18 bears immunologically reactive material 24 which consists, for example, of latex microspheres 1 micron in diameter coated with a suitable immunologically reactive compound, for example, an antibody, or of a bioreactive zone prepared by binding the immunologically reactive compound directly to a solid support consisting of either an activated surface or an inert surface capable of irreversibly binding the immunologically reactive compound.

Assembly 10 is of a diameter suitable for holding membrane 18, for example, 1 cm. Membrane 18 and filter 14 are attached to their respective holders by glue, or other means which prevents leakage between the holder and membrane.

Filter 14 is capable of retaining red blood cells in a mixture of whole blood and salt while allowing passage therethrough of red blood cell-free liquid. Filter 14 can e.g., be a filter having fibers lying on top of one another with a thickness of $\frac{1}{4}$ to $\frac{1}{2}$ mm and a nominal pore size rating of 0.4 microns, for example, a glass AE filter (Gelman). Assay membrane 18 can be any standard assay membrane, e.g., a glass AE filter.

The salt (not shown) is provided in any suitable container, e.g. a cylindrical PVC container, preferably as a buffer solution. The buffer is hypertonic, preferably with an ionic strength greater than 0.5M. In order to reduce the background level of reactivity of the assay membrane with blood solutions, the buffer also contains proteins unreactive with the assay membrane, for example, bovine serum albumin and non-fat dry milk. Preferably, the buffer also contains nonionic detergents, e.g., Tween 80 or Triton X-100 which increase the sensitivity of the assay.

ASSAY

In the first step of the assay, filter 14 is wetted with buffer. Whole blood from the animal or human patient to be tested (approximately 3 drops (0.1 ml)) is gently mixed with 0.5 ml of buffer and the resulting treated whole blood solution is poured into the assembled membrane filter assembly having filter 14 in contact with assay membrane 18. The red blood cells in the blood are retained by the filter, and the red cell-free liquid containing the component to be detected passes through the filter to the assay membrane. After the filtration Process, which takes approximately 1–5 minutes, is complete the filter assembly 12 is removed from the assay membrane and the assay membrane is processed using standard technique to detect the blood component being assayed.

The following example is illustrative.

EXAMPLE A:

Detection of Feline Leukemia Antigen

Antibodies to feline leukemia antigen (commercially available) are bound to latex microspheres by standard techniques and then spotted onto an assay membrane (Gelman AE filter) fixed to a membrane holder as in the FIGURE. A Gelman AE filter is mounted above and in contact with membrane 18, as shown in the FIGURE.

Blood is drawn from a cat by a standard procedure and 3 drops (approximately 0.1 ml) mixed with 0.5 ml of a buffer containing 0.25 molar sodium citrate, one molar KCl, 5% bovine serum albumin, 2.5% non-fat dry milk, and 0.1% Tween 80. The resulting dilute whole blood solution is then poured into the assembly and given 3 minutes to pass through the filter onto the assay membrane. The filter assembly is then removed and the assay membrane treated to determine the presence or absence of feline leukemia antigen using conventional techniques. Generally, after the leukemia antigen has bound to anti-leukemia antibody on the membrane, enzyme-labeled anti-leukemia antibody is added to form a "sandwich", and color is developed using an enzyme substrate and colormetric indicator.

Other embodiments are within the following claims. For example, although it is preferred that the red cell-free liquid be collected on a solid support as described above, the liquid can also be collected in a container and assayed using, e.g., a homogeneous assay method. Any hypertonic solution can be used which causes the required change in shape and deformability of the red cells in the blood, e.g., other salts, and sugar solutions. Any member of a specific binding pair can be measured, for example the assay can be used to screen whole blood samples for HTLV-3 virus or antibodies to this virus to test for Acquired Immune Deficiency Syndrome (AIDS).

I claim:

1. A method for assaying a sample of whole blood for a first member of a specific binding pair, said method comprising treating the sample with a salt to alter the red blood cells in the sample to decrease the ability of the red blood cells to pass through filter media, exposing the treated sample to a filter which retains the altered red blood cells but allows passage therethrough of a sample filtrate, and contacting any of the first member in the filtrate with a second member of the specific binding pair to permit binding of the first member with the second member, whereby said first member is determined.

2. The method of claim 1 wherein said treating substantially increases the rigidity of the red blood cells in the sample.

3. The method of claim 1 wherein the treating step comprises mixing the sample with a hypertonic solution of said salt having an ionic strength at least 0.5M.

4. The method of claim 1 wherein, prior to the step of exposing the sample to a filter, a non-ionic detergent is added to the sample.

5. The method of claim 1 wherein said contacting step comprises contacting the filtrate with a solid support to affix the first specific binding pair member to said solid support.

6. The method of claim 5 wherein said solid support and said filter are in mutual contact when the sample is exposed to said filter.

7. The method of claim 1 wherein the first specific binding pair member is a virus or an antibody against a virus.

8. The method of claim 7 wherein the virus is HTLV-3.

9. A method for assaying feline leukemia antigen in a sample of whole blood, comprising treating the sample with a salt to alter the red blood cells in the sample to decrease the ability of the red blood cells to pass through filter media, exposing the treated sample to a filter which retains the altered red blood cells but allows passage therethrough of a sample filtrate containing the antigen, and contacting any of the first member in the filtrate with a second member of the specific binding pair to permit binding of the first member with the second, whereby said first member is determined.

10. The method of claim 9 wherein the treating step comprises mixing the sample with a hypertonic solution having an ionic strength at least 0.5M.

11. The method of claim 10 wherein said hypertonic solution comprises KCl and sodium citrate.

12. The method of claim 11 wherein said hypertonic solution further comprises nonionic detergent.

13. The method of claim 12 wherein said solution further comprises bovine serum albumin and non-fat dry milk.

14. A kit for assaying a sample of whole blood for one member of a specific binding pair, said kit comprising a first container holding a hypertonic solution, a second container for mixing said hypertonic solution with the sample, a filter positioned with respect to said second container so as to permit a filtrate of said mixture of the sample with said hypertonic solution to pass from said second container through said filter, said filter being capable of retaining the red blood cells in said mixture, and means for collecting the filtrate.

15. The kit of claim 14 wherein said collecting means comprises a solid support.

16. A method for assaying a sample of whole blood for a first member of a specific binding pair, said method comprising:
(a) first forming a solution comprising the sample and sufficient salt to alter red blood cells in the sample to decrease the ability of the red blood cells to pass through a filter media;
(b) exposing said solution to a filter selected retain the altered red blood cells and to allow passage therethrough of a filtrate, said filter being able to pass unaltered red blood cells; and
(c) contacting any of the first member in the filtrate with a second member of the specific binding pair to permit binding of the first member with the second member, whereby the first member is determined.

17. The method of claim 1 or claim 16 in which said filter is wetted with a buffer before sample is exposed to the filter.

18. The method of claim 1 in which said filter is selected to retain the altered red blood cells, to allow passage of a filtrate, and able to pass unaltered red blood cells therethrough.

* * * * *

UNITED STATES PATENT AND TRADEMARK OFFICE
CERTIFICATE OF CORRECTION

PATENT NO. : 4,939,096

DATED : July 3, 1990

INVENTOR(S) : Quentin J. Tonelli

It is certified that error appears in the above-identified patent and that said Letters Patent is hereby corrected as shown below:

Col. 3, line 1, "Process" should be --process--.

Col. 3, line 31, "colormetric" should be --colorimetric--.

Col. 4, line 52, after "selected" insert --to--.

Signed and Sealed this

Tenth Day of September, 1991

*Attest:*

HARRY F. MANBECK, JR.

*Attesting Officer*    *Commissioner of Patents and Trademarks*